United States Patent [19]
Sachse

[11] Patent Number: 6,015,379
[45] Date of Patent: Jan. 18, 2000

[54] ERECTION AID

[76] Inventor: Hans E. Sachse, Lerhenstr. 55, 90425 Nuremberg, Germany

[21] Appl. No.: 08/884,586

[22] Filed: Jun. 27, 1997

[51] Int. Cl.⁷ ...................................................... A61N 5/00
[52] U.S. Cl. .................................. 600/39; 600/38; 602/75
[58] Field of Search ............... 600/37–41; 604/304–307; 242/520; D24/189; 602/1–42, 75–79, 63, 60, 53, 58, 43, 48

[56] References Cited

U.S. PATENT DOCUMENTS

| | | | |
|---|---|---|---|
| 1,216,099 | 2/1917 | Falck | 600/39 |
| 2,085,368 | 6/1937 | Kendall | 128/341 |
| 4,224,933 | 9/1980 | Reiling | 600/39 |
| 4,971,074 | 11/1990 | Hrubetz | 600/39 |
| 5,360,390 | 11/1994 | Maanum | 600/39 |
| 5,370,601 | 12/1994 | Collins | 600/41 |
| 5,522,787 | 6/1996 | Evans | 600/39 |
| 5,667,471 | 9/1997 | Weller et al. | 600/39 |
| 5,843,018 | 12/1998 | Shensol et al. | 602/41 |

FOREIGN PATENT DOCUMENTS

| | | |
|---|---|---|
| 99763 | 4/1925 | Austria . |
| 29603248 | 2/1996 | Germany . |

*Primary Examiner*—Samuel Gilbert
*Assistant Examiner*—Michael Astorino
*Attorney, Agent, or Firm*—Keil & Weinkauf

[57] ABSTRACT

An erection aid for stiffening the male member, which in the position for use is wrapped around the body of the penis and largely covers it, which is in the form of an elastic stiffening band that is stretchable and wherein at least one of the faces of the elastic stiffening band is self-adhesive so that the individual windings of this stiffening band adhere to one another solely by static friction, and so that the bottommost winding of the stiffening band adheres to the skin of the penis by static friction, and which stiffening band further contains rigid reinforcements positioned crosswise to the winding direction and spaced apart from one another.

24 Claims, 10 Drawing Sheets

ERECTION AID

The invention relates to an erection aid for stiffening the male member.

BACKGROUND OF THE INVENTION

In the absence of capability of erection or with severely impaired erection, in order nevertheless to achieve the capability of having intercourse, quite various means and methods have been employed up to now, but all of them have disadvantages. Stiffening the penis surgically, for instance, by implanting a so-called penile prosthesis, is unacceptable to many men because of the constant problems this often entails. Moreover, these usually quite expensive devices frequently fail to become properly incorporated. Methods for erection improvement by means of injections of medications into the corpus cavernosum of the penis or by introducing medications into the urethra just before intercourse are also known. Methods and experiments are also known for constricting venous drainage from the corpora cavernosa, thus damming the flow, by placing a ring around the root of the penis, as in German Utility Model DE 296 03 248 U1, in order thereby to increase the turgor in the corpora cavernosa. U.S. Pat. No. 5,234,401 addresses similar problems, using a tube placed in airtight fashion against the root of the penis and creating a negative pressure in the tube that is intended to increase the volume of the penis. The air produced by creating the negative pressure is pumped into a ring that is seated at the root of the penis and that when inflated is intended to reduce venous return. However, all the above known versions assume good, intact arterial flow to the penis. But this condition no longer exists in men whose prostate has had to be entirely removed (radical prostatectomy) because of cancer. In that case—with few exceptions—the main arteries and nerves of the penis that are indispensable to erection of the corpora cavernosa of the corpus penis have been severed. These corpora cavernosa of the corpus penis, or cavernous bodies of the body of the penis, are then no longer functionally available for purposes of erection. Conversely, the arterial and neural supply to the corpora cavernosa of the glans penis (glans) is usually still intact. Thus a man who has had radical prostate surgery but whose testicles have not been removed, has both the desire for intercourse and a certain capability of erection on the part of his glans. But he lacks the stiffening of the corpora cavernosa of the body of the penis and is thus incapable of performing intercourse. He can be helped only by a stiffening device placed around the body of the penis.

Devices for stiffening the penis from outside are known and are described, in German Patents DE 37 23 746 C2 and DE-OS 875,853, German Utility Model DE 72 43 079 GbM, and U.S. Pat. Nos. 5,360,390, 5,513,652 and 4,785,802, as more or less tubular sheaths, liners and the like which thus act as braces for the body of the penis. These sheaths are largely rigid and if they are to be correctly applied must be individually selected from a great assortment of different sizes. Once applied, the inside diameter of these bracing devices cannot be changed again to adapt to the volume and turgor of the body of the penis. If the body of the penis is overly compressed when such a device is put in place, there is the risk of circulatory disturbances. The degree of repletion of the corpora cavernosa of the body of the penis and of the glans fluctuate very markedly, especially at the moment of sexual arousal, even in the man who has undergone surgery. If the degree of repletion, the turgor pressure, and thus the diameter of the glans decrease, then the glans can slip into the rigid tubular stiffening device during intercourse and thus prevent intercourse from continuing. It appears very questionable whether this possibility can be prevented by means of a greatly constricted "orifice" as in DE 37 23 746, because of the attendant risk of injury and the danger of paraphimosis.

In German Patent DE-PS 134 368, the body of the penis is stiffened by wrapping a "bandage-like strip of fabric, covered on the inside by an adhesive composition" around it. Admittedly this fabric is meant to be flexible and elastic. But adhesively bonding these lengths of fabric strips to one another and to the penis means that in use, i.e. during intercourse, this elasticity is in fact lost. On the contrary, once again the result is a firm, inelastic tube with the above-described disadvantages, which the invention seeks to overcome. Although the aforementioned adhesive bonding means that the skin of the penis can be glued to the inside face of the wrapping, still given the very loose connective tissue between the skin of the penis and the underlying corpora cavernosa, which make up the actual volume of the body of the penis, the corpora cavernosa can still retract into the wrapping, along with the glans that is joined to them. Such a retraction could be avoided only by means of a very taut wrapping. But in that case, a layer of adhesive would be more a hindrance than a help. It makes the wrapping hard to handle and does not allow any corrections to be made as the wrapping is being wound into place.

BRIEF DESCRIPTION OF THE INVENTION

In view of the above prior art, the object of the invention is to create an erection aid that is easy to handle, that makes do without using medications and without surgical intervention, and that takes into account the variable degree of engorgement of the penis of a user.

To attain this object, first in an erection aid that is wrapped around the body of the penis in the position for use in order to stiffen the male member (DE-P5,134,368), it is provided in accordance with the present invention that the erection aid comprises an elastic stiffening band that can be wound around the body of the penis of a user and that is stretchable, in which the individual windings of this stiffening band adhere to one another solely by static friction; moreover, and static friction also exists between the bottommost winding of the stiffening band and the skin of the penis, and that rigid reinforcements disposed crosswise to the winding direction and spaced apart from one another are provided. The windings of the stiffening band, by its design and/or material, not only stick together without any adhesive but are also displaceable relative to one another if pulled relatively hard. The stiffening band is wrapped around the body of the penis in the circumferential direction, thereby adapting to the current volume and turgor of the body of the penis. In applying the device, the man can increase the pressure on the body of the penis with each winding, or if the pressure becomes too high he can partly or completely unwrap it and arrive at the proper application pressure with a new winding. The firm adhesion to the body of the penis is effected by means of the individually metered pressure with which the stiffening band is applied. In particular, this makes it possible to adapt to variably pronounced tumescence of the body of the penis. The extent to which the body of the penis is covered and stiffened by the stiffening band is variable. It is recommended that the height of the stiffening portion be dimensioned such that the essential length of the body of the penis is encompassed by it.

The reinforcements can comprise plastic strips, stiff textile strips, metal, etc., and are glued onto the elastic stiffening band, sewn on, packed in pockets, or woven into the stiffening band itself. It is highly advantageous if, according to this claim, the elasticity of the stiffening band is preserved in between the reinforcements. The spacing of these reinforcements to one another can then differ. For example, this spacing may be approximately equivalent to the width of the reinforcements. However, it may also be so slight that the band appears uniform. In another embodiment of the invention adhesive strips are provided, which secure the self-adhesion of the ends of the band even in the face of relatively major strain.

In accordance with another embodiment of the invention strips of self-adhesive elastic material are located at the beginning and at the end of the stiffening band. In this version of the embodiment, the strips of the beginning of the band and of the end of the band are wrapped around the cp in opposite directions from one another and pulled taut, so that they come to be located as shown in FIG. 4. Since the radical prostatectomy patient no longer has tumescent corpora cavernosa of the body of the penis, these bodies can be simulated in accordance with another embodiment of the invention. The missing corpus cavernosum volume is compensated for by providing that cylindrical stiffening elements that imitate the shape of the corpora cavernosa are incorporated into the stiffening band.

Further embodiments of the invention include possible ways of embodying the stiffening band to engender adequate adhesion between windings on top of one another, as well as between the bottommost winding and the skin of the penis, without having to use adhesive materials. Textile bandages with a woven structure are known, but in a different field of art from the present erection aid attained by means of an elastic stiffening band.

The use of condoms in conjunction with erection aids is known in the prior art discussed at the outset above. In a further embodiment of the invention, the advantage is attained that one end of the condom comes to be located in the vicinity of the Sulcus coronarius (cervix of the penis), while the other end comes to be located in the vicinity of the root of the penis. In this condomlike sheath, the glans remains exposed, to preserve its sensitivity. The use of a condom that has a perforation extending all the way around in the region of the Sulcus coronarius would also be conceivable, so that after the condom is in place, the part of the condom that covers the glans can be removed by tearing it off at the perforation.

However, a longer condomlike sheath can also be applied in such a way that, it comes to be located both between the skin of the penis and the inside of the stiffening band, and on the outside of the stiffening band. It application is meant to be made easier by providing the condomlike sheath in the form of a double winding that is mounted on a plastic ring. First, the winding oriented toward the root of the penis is rolled onto the body of the penis; then the stiffening band is applied; and after that, the winding oriented toward the glans is rolled down over the stiffening band toward the root of the penis. In this embodiment, only the stiffening band is completely covered by the condomlike sheath and is secured against slipping by the stiffening band.

In the embodiments of the invention discussed thus far, only the body of the penis is stiffened; its erectile position relative to the body has not been addressed. When the man is upright, the member remains more horizontal than not, or points obliquely downward.

Further embodiments of the invention relate to the addition of a bracing part which enables a "physiological" position of the member in the aroused state.

In order to make it easier to apply the stiffening band or to improve features it is possible to reinforce the initial part or the edges of the stiffening band or to provide the stiffening band with a suitable opening into which the the initial portion of the stiffening band can be inserted for use.

In another embodiment of the invention a stiffening band after being fitted over the body of the penis, is disposed in a spiral and slides into itself when pressure is exerted from outside. This decreases the inside diameter of the spiral until the correct contact pressure against the body of the penis is attained.

In accordance with a further preferred embodiment, as it is slipped over into itself the band is guided by U-shaped hoops and is prevented from shifting away from the intended direction.

In accordance with another embodiment of the invention the erection is a stiffening band which while not stretchable can be flexibly wrapped around the body of the penis. It comprises two halves, joined together by a bandlike bridge, which on the inside face have cushions placed on them that can be filled with air or a liquid medium. After this stiffening device is wrapped around the body of the penis, the cushions are filled with air through filling conduits, in a way similar to what is done with a blood pressure cuff. By filling it to a variable extent, the correct contact pressure is attained and the erection aid is secured on the body of the penis.

Further advantages and characteristics of the invention can be found both in the other dependent claims, whose content is hereby expressly incorporated by reference, and in the ensuing description and the associated drawings of possible embodiments according to the invention.

Shown in the essentially schematic drawings are:

DETAIL DESCRIPTION OF THE DRAWINGS

Figure 1:
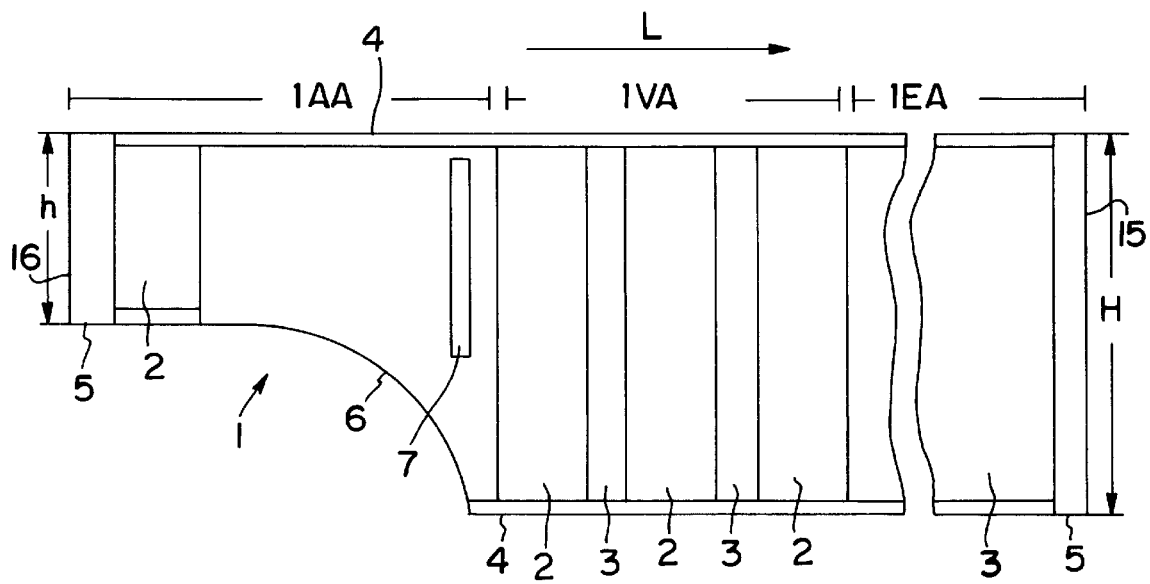
FIG. 1: a plan view on a bandlike stiffening device according to the invention in the flat state, i.e. not wound around, looking at the face that will later rest on the skin of the penis.

The reference numerals used in the drawings are designated as follows:

| | |
|---|---|
| (1) | Elastic stiffening band |
| (2) | Reinforcement |
| (2') | Reinforcement (strip) |
| (3) | Elastic portion |
| (4) | Narrow folded-over edge |
| (5) | Adhesive strip |
| (6) | Curved tapering of the lower edge |
| (7) | Slit |
| (8) | Glans penis (glans) |
| (9) | Body of the penis |
| (10) | Sulcus coronarius (cervix of the penis) |
| (11) | Beginning of supplementary band |
| (12) | End of supplementary band |
| (14) | Root of the penis |
| (15) | Edge of terminal portion of stiffening band |
| (16) | Edge of initial portion |
| (17) | Stiffening elements, imitation corpora cavernosa |
| (18) | Urethra |
| (19) | Bendable stabilizing element |
| (20) | Hinge region |
| (21) | Boundary between 1AA and VA |
| (22) | Boundary between VA and EA |
| (23) | Condomlike sheath open at both ends |
| (23') | Condomlike sheath open at both ends for covering both sides of the stiffening band |
| (24) | Terminal bead of 23 |
| (25) | Wound region of 23' in the direction of the root of the penis |
| (26) | Wound region of 23' in the direction of the tip of the penis |
| (27) | Wrapping 25 rolled onto the penis |
| (28) | Plastic ring as a carrier ring |
| (29) | Relatively stiff, longitudinally non-stretchable stiffening band |
| (30) | Initial portion of 29 |
| (31) | Terminal portion of 29 |
| (32) | Inside face of 29 |
| (33) | Outside face of 29 |
| (34) | Direction of pressure on 29 |
| (35) | Inflatable erection aid in the form of a cuff for the body that can be pumped up |
| (36) | Filling conduit for 47 with valve closure |
| (37) | Annular bracing part for the stiffening band |
| (38) | Hinge of the bracing part |
| (39) | Continuation of the bracing part |
| (40) | Bristles or fine hairs, top side |
| (41) | Bristles or fine hairs, underside |
| (42) | Bracing part in perineal region |
| (43) | Bendable region of 19 |
| (44) | Perineal-scrotal region |
| (45a) and (45b) | Stiff halves of the band |
| (46) | Bandlike connection of 45a and 45b |
| (47) | Small inflatable sacs |
| (48) | Stiffening portion of the band |
| (49) | Retaining strip |
| (50) | Adhesive layer |
| (51) | Seam |
| (52) | Sewn pocket |
| (53) | Metal reinforcing wire -- |

The embodiment of the invention in FIG. 1 has a preferably one-piece stiffening band 1, which comprises two successive portions 1AA, 1VA and 1EA; specifically, AA designates the initial portion, VA the stiffening portion, and EA the terminal portion. The application to the penis is done such that first the initial portion 1AA is wound around the body of the penis, and its upper edge, in terms of FIG. 1, comes to rest in the cervix 10 of the penis, below the edge of the glans. The narrow edge at the beginning of this portion 1AA can be provided with a self-adhesive or pressure-sensitive adhesive strip 5. There as well, a reinforcement 2' may be provided, as indicated by cross-hatching. The height h of this initial portion of the stiffening band may preferably be less than the height H of the portions 1VA and 1EA. The portion 1AA increases continuously in height, from the initial portion of height h to the beginning of the portion 1VA of height H. To that end, the lower edge 6, in terms of the drawing, may have a curved course. In applying this stiffening band, it is easier, using this initial portion 1AA, to wind a part that has no reinforcements, and is therefore both relatively thin and also flexible and elastic, and that not until its terminal region, that is, at the transition to the portion 1VA, around the penis perfectly, without any interstices. This averts the risk that, if the stiffening band is applied carelessly, the glans can slip into the stiffening device. On the contrary, as shown in FIG. 1 this portion 1AA is seated tightly, solidly and elastically on the skin of the penis. A slit 7 may also be provided in the region of the band near the stiffening portion 1Va. The initial region of the portion 1AA can then be inserted into this slit to make application easier.

The stiffening portion 1VA, in this example, has a plurality of reinforcements 2, which can extend over it full height and which, as explained for the other exemplary embodiments, may be variously embodied. The elastic intermediate portions 3 between the reinforcements 2 make the device easier to apply and wrap around the body of the penis. The reinforcements 2 in the possible embodiments of FIG. 1a may comprise a textile-, plastic- or rubberlike material, or metal. Expediently, the longitudinal direction of the band, as FIG. 1 also shows, extends in the direction of the total length L, so that the reinforcements are disposed at right angles to this longitudinal or winding direction (see the directional arrow L in FIG. 1). To adapt to different lengths of-penis, stiffening devices according to the invention of different heights H may be provided. By way of the above-described reinforcements 2 of the band alone, there is already the capability of intercourse, but an erectile position is not yet assured. In the aforementioned longitudinal or winding direction L, one portion of the elastic stiffening band and a rigid reinforcement alternate with one another. The width of these respective portions should be determined on a case by case basis. The width of the elastic portions, for example, may be equal to the width of the reinforcements. However, it is also possible to keep the spacing of the reinforcements from one another so slight that the elastic regions are hardly visible any longer; in other words, such a stiffening band appears uniform.

The embodiment of FIG. 1 could also be realized in such a way that the entire initial portion 1AA has the same height H as the stiffening portion 1VA and the terminal portion 1EA. For the reasons noted, however, preference is given to the version described above and shown in FIG. 1, in which the height h of the beginning of the initial portion 1AA is less than the height H of the ensuing portions 1AA and 1EA.

The design and/or the material of the elastic stiffening band is such that its individual windings adhere to one another solely by static friction, and static friction also exists between the bottommost winding of the stiffening band and the skin of the penis. This can be attained by providing that the two faces of the stiffening band have both outward-protruding and complementary indented regions, which enables the aforementioned adhesion. This design may be in the form of a woven structure, for instance. Such a stiffening band may comprise this kind of woven textile material, or suitably formed or impressed plastic or rubber strips. The material of the stiffening band 1AA–1EA may be folded over at its edges by the flap 4. The thus-strengthened edges make handling easier. An adhesive strip 5 may be applied to the terminal region of the stiffening band as well.

Figure 1A:
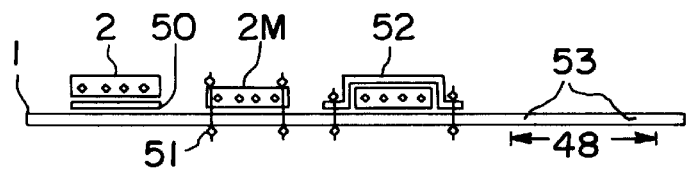
FIG. 1a: a cross section through a stiffening band with reinforcements applied.

FIG. 1a shows a schematic cross section through the stiffening band 1 with various options for securing the reinforcements 2. For instance, the reinforcement 2 may be secured to the stiffening band by means of an adhesive 50; at 51, it is sewn on, and at 52, it is accommodated in a pocket. In FIG. 1a on the right, a portion 48 of the elastic stiffening band is shown. Metal wires 53, whose cross sections are visible, are embedded in it as reinforcements (for the sake of simplicity in the drawing, reference lines are drawn only to the cross section on the left and that on the right, but not to all the intervening cross-sectional views of these reinforcing wires).

The self-adhesive embodiment of one or both faces of the stiffening bands according to the invention can be accomplished in various ways. For example, they may be Velcro-like adhesion-promoting means (not shown). A self-adhesive embodiment in a woven structure is also possible, of the kind known in elastic bandages. The stiffening band may comprise a fabric (textile), or it may also comprise rubber or plastic.

Figure 1B:
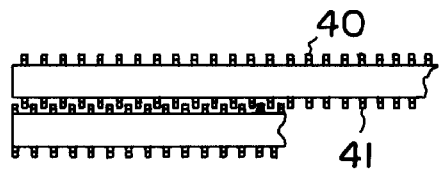
FIG. 1b: a longitudinal section through two portions, joined by sticking together, of the stiffening band.

FIG. 1b in this regard shows the stiffening band, which is provided on both sides, i.e. on both faces, with bristles or fine hairs 40, 41, which protrude vertically from the respective sides and mesh adhesively (see FIG. 1b, left-hand half). This adhesion can be undone by pulling on it appropriately, and can be restored again by exerting suitable pressure.

Figure 2:
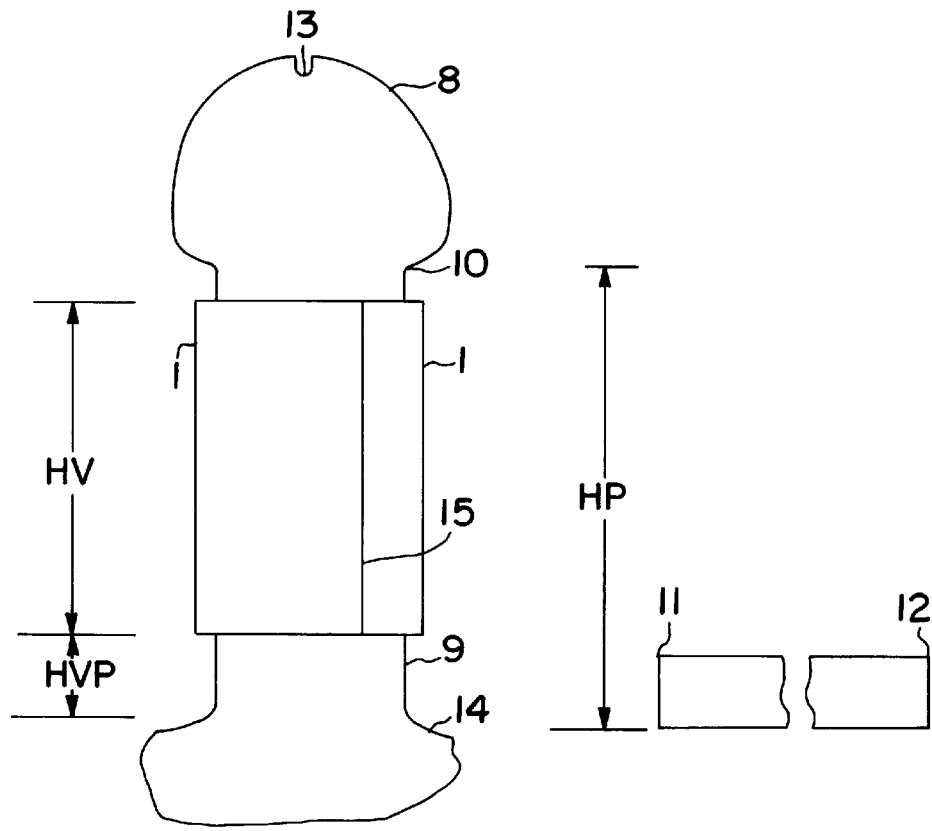
FIG. 2: a side view of the penis with the stiffening band of FIG. 1 wrapped around it.

FIG. 2 shows a side view of a penis with a stiffening band applied. In this exemplary embodiment, there is an well-defined interstice between the cervix and the edge of the stiffening band, and also between the root of the penis and the edge of the stiffening band. This view is intended to demonstrate that the reinforcement 1, because of its elastic properties, adheres to the body of the penis 9 and does not exert any bracing function on the glans 8. In this example, the height HP, which is equivalent to the spacing of the cervix 10 from the root of the penis 14, is markedly greater than HV, which is the width of the stiffening band. A supplementary band with two end edges 11 and 12 can also be provided, as shown at bottom right in FIG. 2. This supplementary band, if needed, is wound around the body of the penis in the region HVP. There, it represents a further lengthening of the stiffening band 1 and of its bracing against the body (root of the penis 14). Thus for stiffening a longer penis, the supplementary band is used. To apply the stiffening band and the supplementary band, the penis can be stretched by pulling on it. Once the supplementary band is in place and the penis is let go, perfect bracing is provided because of the supplementary band.

Figure 3:
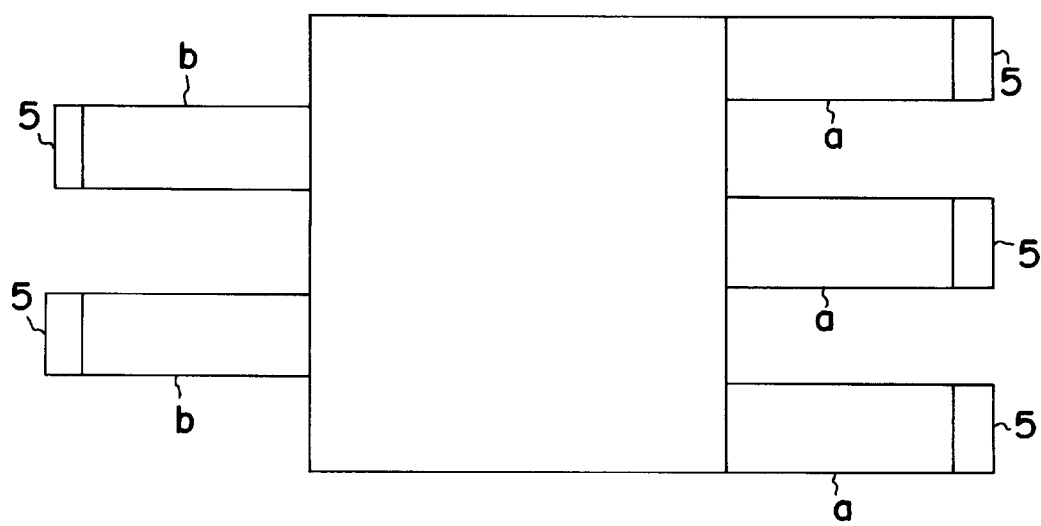
FIG. 3: a plan view of a further version of a stiffening band, shown flat rather than wound around.
Figure 4:
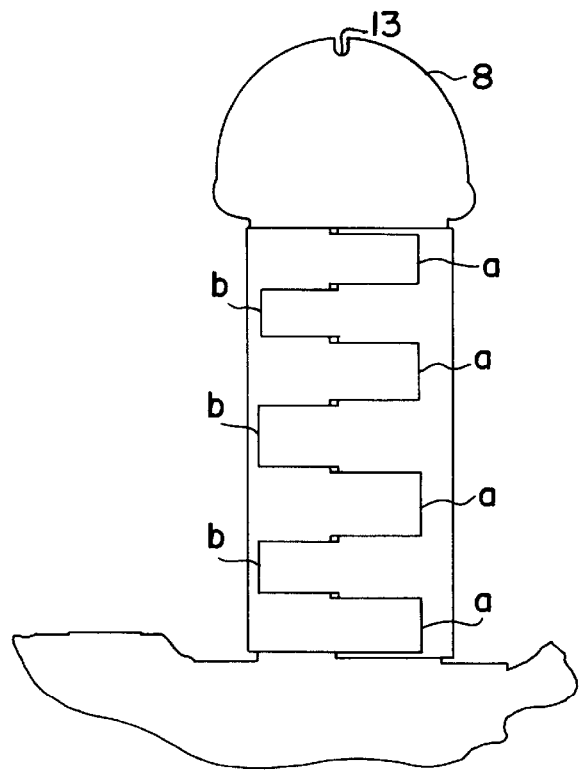
FIG. 4: the side view of a penis with a stiffening band wrapped around it analogously to FIG. 3.

FIGS. 3 and 4 show a version of the invention in which there are retaining strips a and b on the stiffening region 1VA of FIG. 1; once this stiffening region has been placed around the penis, these retaining strips rest from outside on the stiffening region 1VA. The retaining strips a, on the right in FIG. 3, and b, on the left in FIG. 3, are positioned such that when the stiffening band has been wrapped around the penis they do not overlap but instead each fit into the gaps present between the strips of the respectively other side.

FIG. 4 shows the side view, relating to FIG. 3, with the intermeshing strips a and b, which as indicated by being dotted differently are different from one another.

Figure 5:
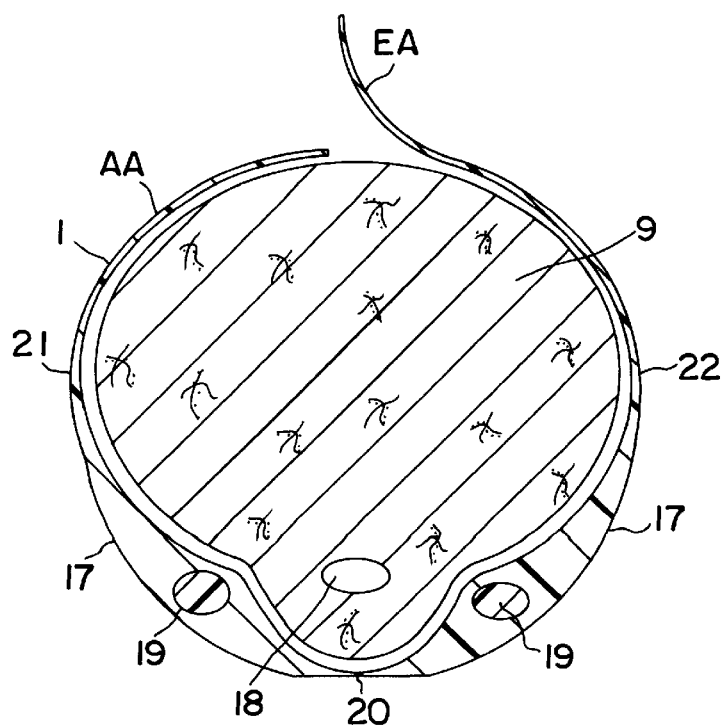
FIG. 5: a sectional view of the body of the penis with a further version of a stiffening band with an embedded stabilizing part.

FIG. 5 shows a further possible embodiment of the invention, in which shell-like, cross-hatched stiffening elements 17 are located only in the region indicated of the stiffening band 1a. As in the previous exemplary embodiments, it is provided in this embodiment of the invention as well that this stiffening device be wrapped around the penis in the circumferential direction of the body of the penis, because the thickening of the glans penis makes it is impossible or at least impracticable to slip the device onto the penis longitudinally.

In this exemplary embodiment of FIG. 5, the stiffening band 1 with the cylindrical stiffening elements 17 is folded open in the region 20 and applied to the body of the penis 9 from below. In this exemplary embodiment as well, the stiffening device is then wrapped around the body of the penis in the circumferential direction, again avoiding a disadvantageous or impracticable application longitudinally onto the body of the penis.

In their position and form, the stiffening elements 17 extending longitudinally of the penis or in the direction of the height H of the stiffening band may simulate the corpora cavernosa, which (as noted above) are functionally no longer in existence in a man who has had a radical prostatectomy, and which are replaced in this embodiment of the invention by the reinforcements 17.

Figure 6:
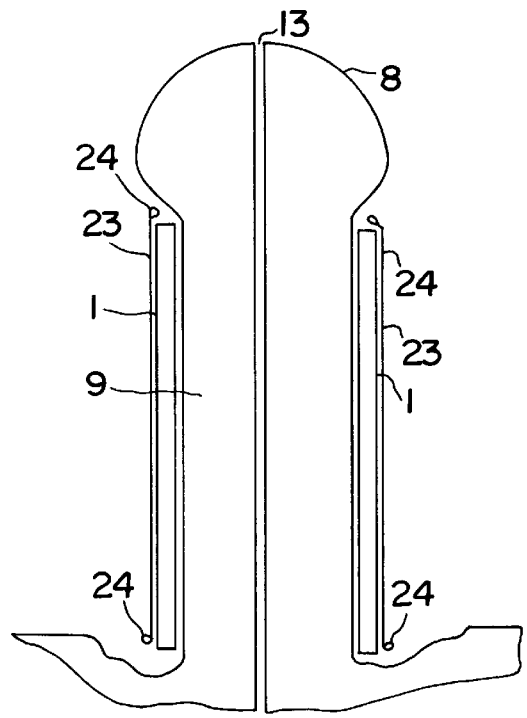
FIG. 6: a longitudinal section through a penis with a stiffening band and a condomlike sheath.
Figure 7:
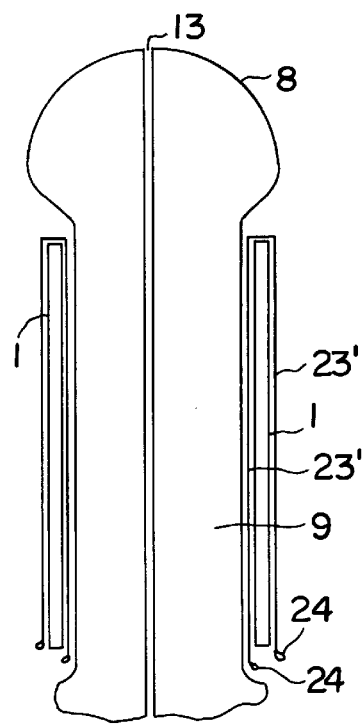
FIG. 7: a longitudinal section through a penis with a stiffening band and another version of a condomlike sheath.
Figure 8:
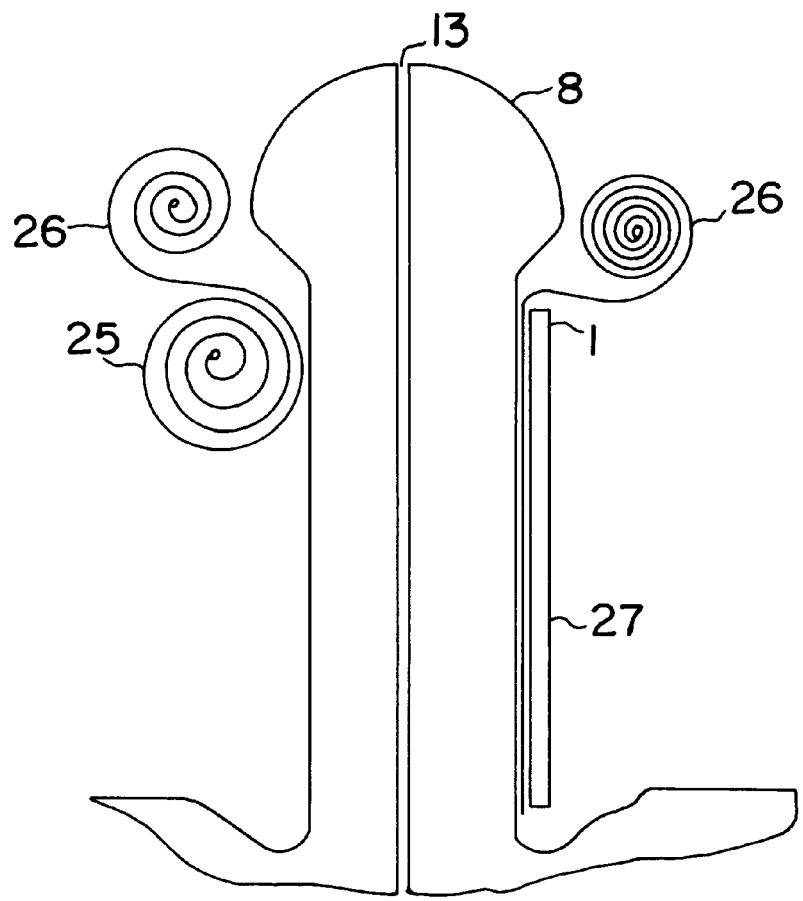
FIG. 8: the arrangement of FIG. 7, in which at first the condomlike sheath is only partly in position.
Figure 9:
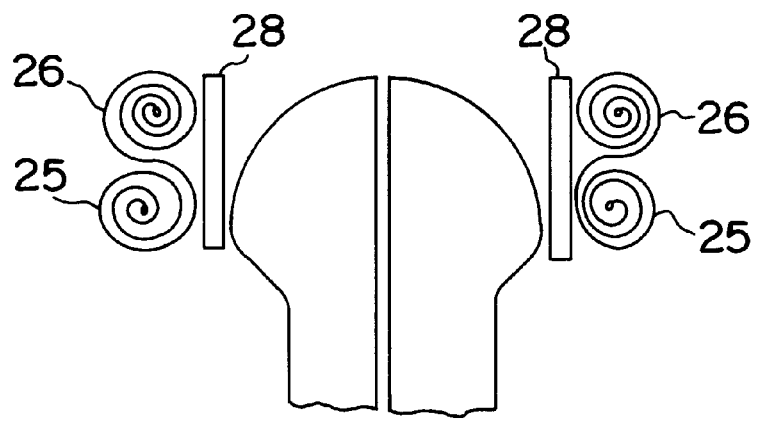
FIG. 9: an auxiliary device (28) for applying a condomlike sheath with a double winding.
Figure 14:
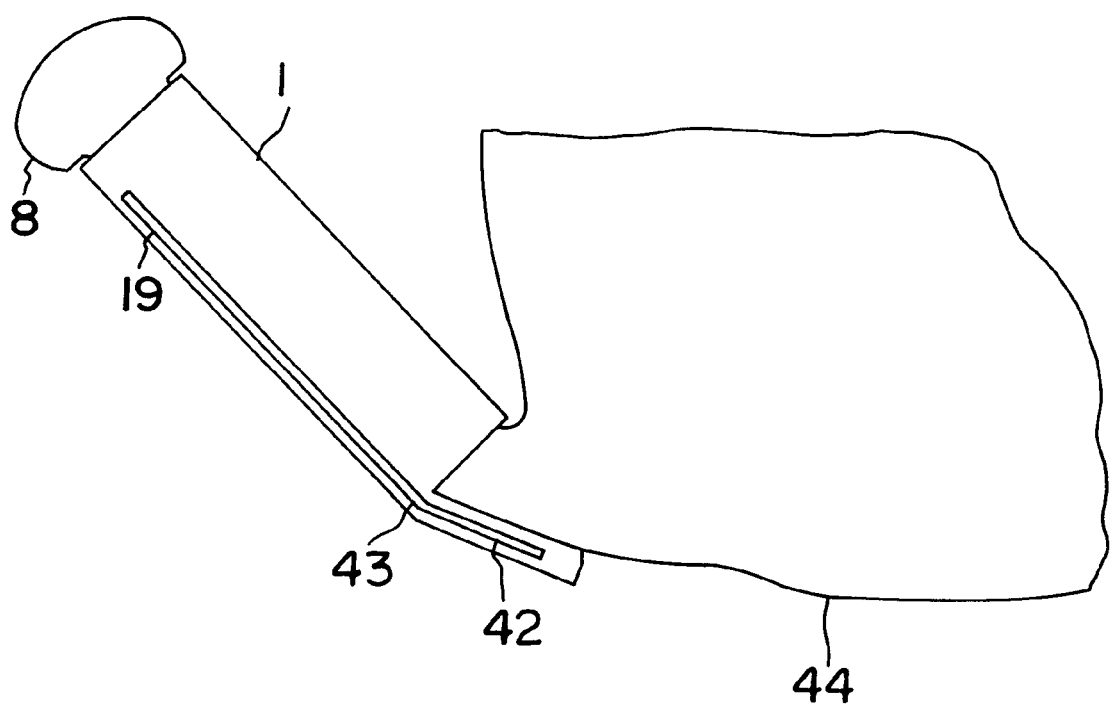
FIG. 14: a side view of the penis with a bracing device.

FIG. 5 also shows bendable stabilizing elements 19, inside the reinforcements 17, which likewise extending longitudinally or in other words over the height H of the stiffening device and can continue beyond that in the form of the bracing parts 42 of FIG. 14. Although a complete, conventional condom may be applied over a penis that has been provided with a reinforcement according to the invention, still it is the subject of the invention the provide a condomlike lining or sheathing of the stiffening device only, while conversely the glans penis is left free of this sheathing. The glans penis thus remains exposed for coitus, which is important for the sake of preserving full sensitivity. One such condomlike sheath 23 can be seen in FIG. 6, with reinforced edges 24. In the version of FIG. 7, this sheath can be located either on the outside of the stiffening region 1 as indicated by reference numeral 23, or on the inside thereof, as indicated by reference numeral 23', i.e. between the stiffening band and the body of the penis 9. In this regard, FIG. 8 shows, on the left, how a condomlike sheath comprises two contrarily wound regions 25 and 26, of which 25 is first drawn over the body of the penis into the position shown on the right in FIG. 8. Beforehand, that is before this condomlike sheath has been unrolled, it was placed, after being stretched with the fingers, in the cervix region. After the lower wound region 25 is unrolled, the stiffening band 1 is applied and then the upper wound region 26 of the sheath is wound downward over the stiffening band 1 until the position shown in FIG. 7 is reached. This positioning and application of the sheath 25, 26 is also possible, as shown in FIG. 9, by premounting this special sheath on a plastic ring 28, whose inside diameter is somewhat larger than the outside diameter of the glans, the sheath being seated with tension on the ring. Once the aforementioned plastic ring has been slipped over the glans, the condomlike sheath 25, 26 is pushed downward onto the cervix and the plastic ring 28 is removed. After that, the unrolling of the special sheath and the application of the reinforcement are done as already described above. The plastic ring 28 may have small peripheral beads on its end regions, to prevent the sheath from slipping off unintentionally. Leaving the glans penis free as noted above can also be achieved with a condom that has an annularly encompassing perforation at the appropriate point. Once the condom is slipped on, its portion that covers the glans penis is then torn off.

In the possible embodiments of FIGS. 6–9, a tube of a very thin, elastic material, open at both ends and optionally provided with bulbous tips 24, is used.

Figure 10:
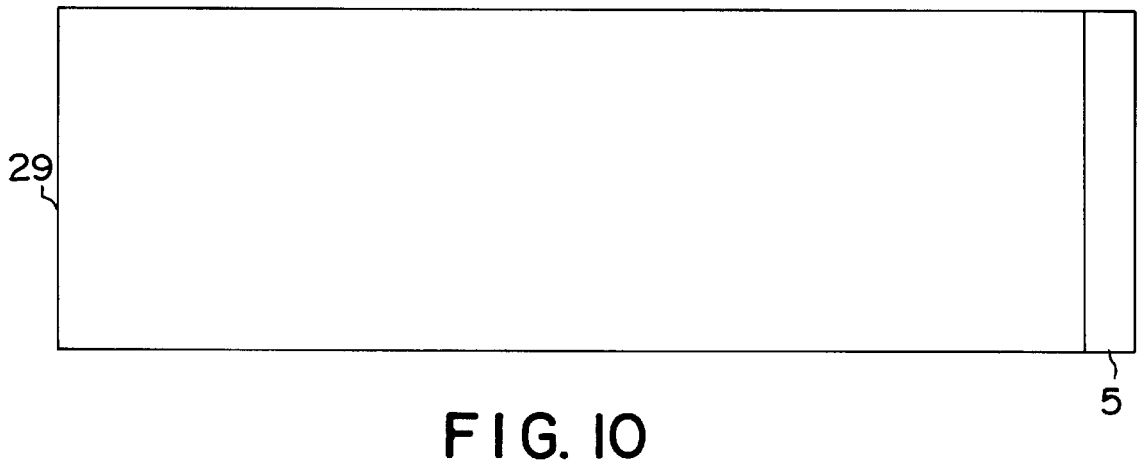
FIG. 10: a further embodiment of the invention in a plan view of the face that will later rest on the skin of the penis.
Figure 11:
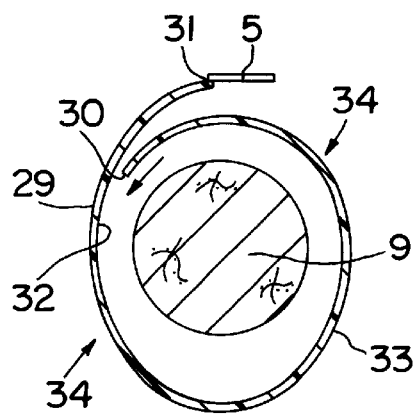
FIG. 11: a cross section through the penis with the stiffening device of FIG. 10 not yet fully applied.

The exemplary embodiment of FIGS. 10 and 11 shows an intrinsically one-piece band of a relatively stiff material, which is embodied as smooth-walled or smooth on the outside and/or inside. This stiffening band 29 is wrapped loosely at first in a spiral around the body of the penis 9, as FIG. 11 shows. By exerting pressure in the direction of the arrow 34, the leading edge 30 of this band 29 is made to slide along the smooth inside face 32 of the band, until the band over its entire length, surrounding the body of the penis, rests solidly thereon so that it adheres to the body of the penis without shifting. This sliding into itself of this stiffening device—in the manner of a wide spiral spring—can be facilitated by means of U-shaped retaining devices, not shown, on the edges.

The smooth design of the inside faces 32 and outside faces 33 of the band 29 can be attained in various ways, such as by a suitable choice of the material of this band, or by means of a plastic sheath. Since as explained this band intrinsically has a reinforcing strength, it would also be conceivable to make it from a plastic strip of suitable stiffness; the smoothness of a plastic surface would then be exploited to attain the described wrapping that sits solidly on the penis 9 and on itself. To keep the wrapping in this position, an adhesive strip 5 or a Velcro closure may be provided on the end region.

Figure 12:
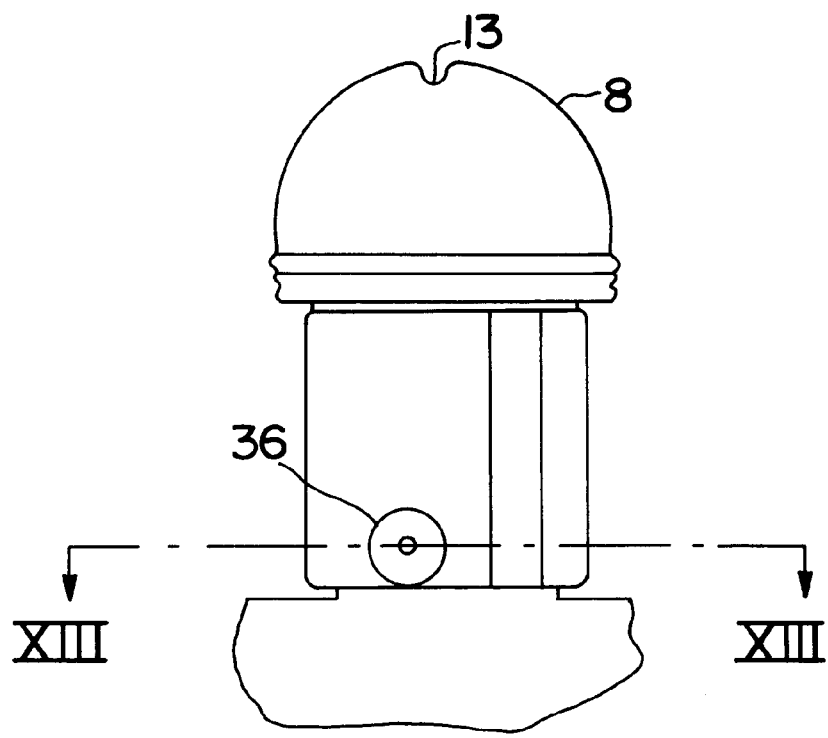
FIG. 12: a further possible embodiment of the invention, in a side view.
Figure 13:
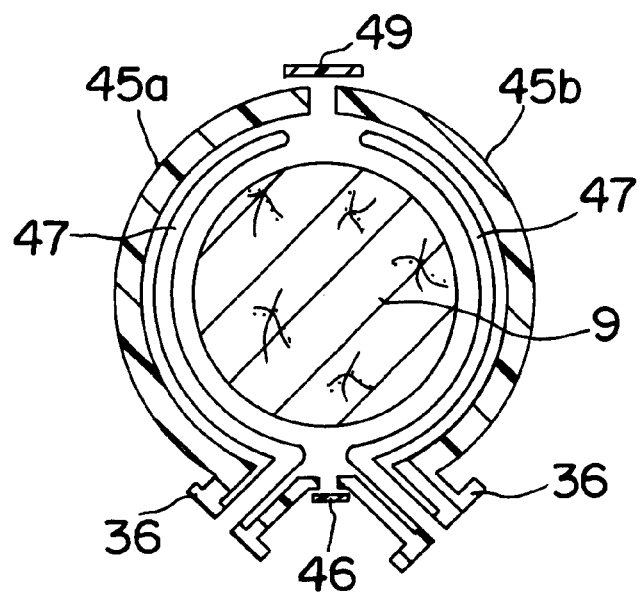
FIG. 13: a cross section taken along the line XVII—XVII of FIG. 12.

FIGS. 12 and 13 show the penis with an inflatable erection aid 35, by means of which, in the bandlike connection 46, there are relatively rigid halves 45a and 45b of the band joined movably to one another, on whose inside there are small inflatable sacs 47, on the order of a blood pressure cuff. By means of one supply line per sac, the line having a valve 36 and being located in the region of the root of the penis 14, air can be pumped into the sacs until such time as they sit tightly against the body of the penis. Once the device is wrapped around the body of the penis, the two halves 45a, 45b are held together by the retaining strips 49.

If necessary, the versions shown in FIGS. 10–13 can also be sheathed with a condomlike sheath. In general, the characteristics shown for one of the exemplary embodiments can be used in one of the other exemplary embodiments as well, if possible and appropriate.

FIG. 14 shows another exemplary embodiment, in which the stiffening band 1 of FIG. 1 is extended by the stabilizing part 19 to form a perineal brace 42.

The stabilizing part 19 preferably comprises a bendable metal element. The bending angle, shown at 43, of this stabilizing element determines the orientation of the erect member. The bending point 43 is located at the transition from the stiffening band to the bracing part 44. In the preceding exemplary embodiment, the stiffening band is integral with a bracing part 42. However, the bracing part 42 could also be a separate part (not shown in the drawing), by having a plug-type connection with the stiffening device that on the one hand makes the aforementioned connection and on the other, at the same time, also brings about the desired bending angle (see above). It can be inferred from this that the bracing parts 42 are braced against the perineum 44 of the body of the man and thus keep the penis and the stiffening device in the position that an erect male member assumes.

Figure 15:
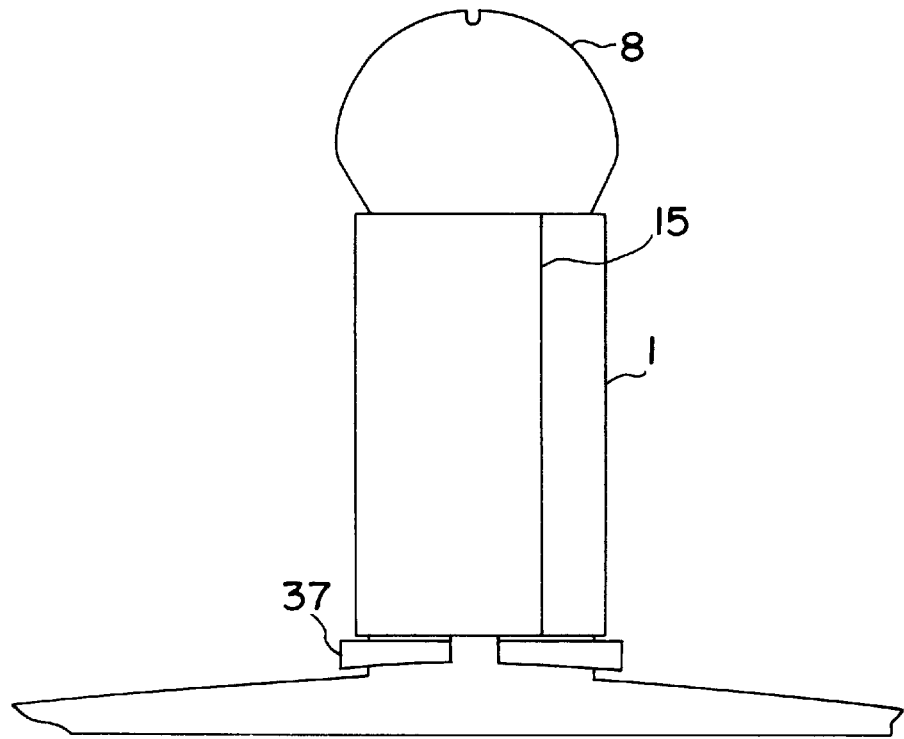
FIGS. 15, 16 and 16a: further possible embodiments of the invention with braces at the root of the penis.
Figure 16:
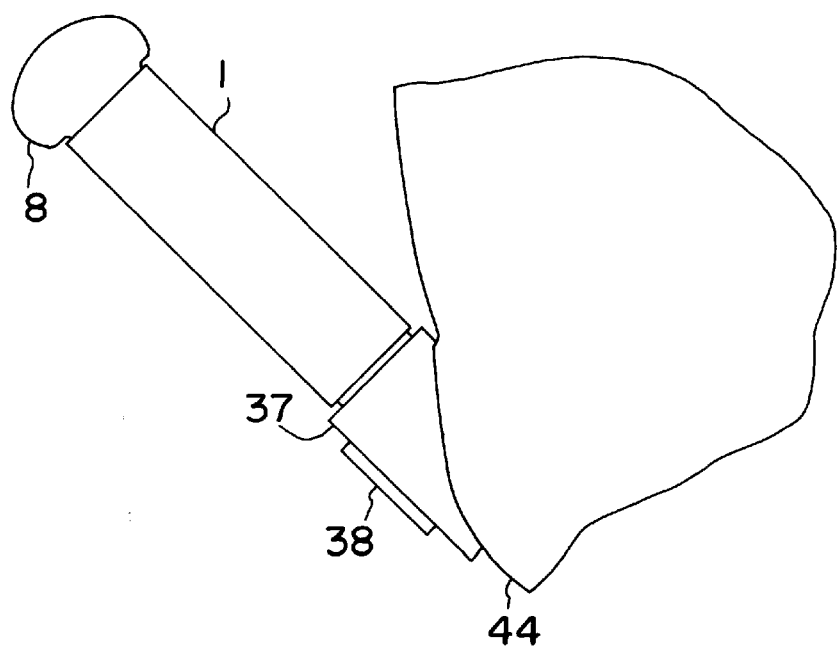
Figure 16A:
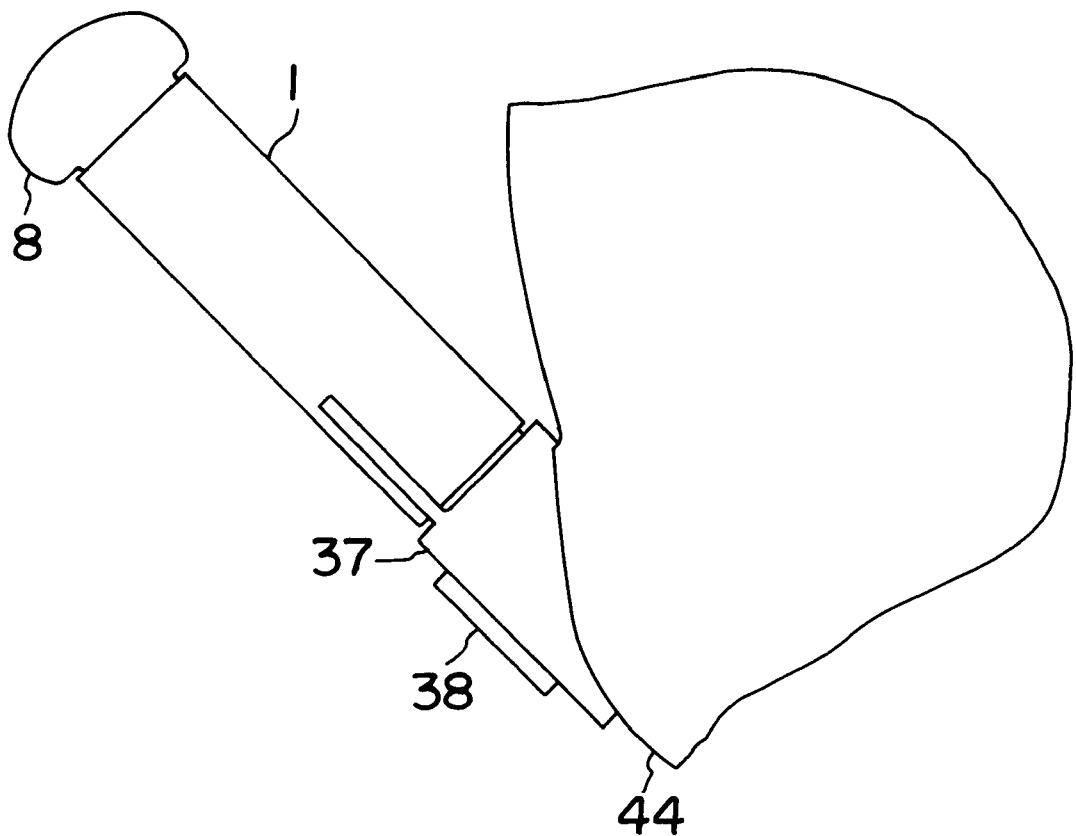

A further exemplary embodiment of a bracing part 37, on which the stiffening band 1 can be braced, is shown in FIGS. 15, 16 and 16a; FIG. 15 shows a plan view on the annular bracing part looking toward the perineum, FIG. 16 shows the associated side view, and FIG. 16a shows a variant of the aforementioned arrangement.

The bracing part 37 annularly encompasses the root of the penis, in the manner of a split ring, whose width increases sharply toward the scrotal-perineal region 44 and is configured as almost "wedge-shaped" when seen from the side. This bracing part 37 may be a single piece of highly elastic material. For further stability, it is wrapped around the penis and then secured with a retaining band or the like. Instead, the bracing part may comprise two halves, which are movably joined together by a hinge 38 or by means of a band. Folded open, the bracing part 37 can be wrapped around the root of the penis from underneath. The bracing part 37 can then be held together at the top with a retaining device, not shown, such as an adhesive strip. The bracing part may also comprise a single piece of material which in particular is stiff, which is wrapped around the penis and kept in this position with a Velcro closure. Such a bracing part may also comprise a textile material, or a plastic "skeleton" provided with a suitable textile sheath. Once the bracing part is applied, the stiffening band may sit by simple contact on the end face, pointing toward the penis, of the bracing part 37 and the desired "normal" erectile orientation can be gained thereby. It is also possible to extensions 39 of the bracing part 37 to be incorporated into the wrapping. This lends a firmer hold. These extensions 39 are preferably located toward the perineum. Compared with the exemplary embodiment shown in FIG. 14, the bracing part 37 achieves very good bracing on the root of the penis. Slipping away sideways is no longer possible. A combination of the two forms of bracing is also conceivable.

All the novel characteristics shown and/or described, and their combinations with one another, are considered to be essential to the invention.

I claim:

1. An erection aid for stiffening the male member, which is adapted to be wrapped around the body of the penis and to largely cover it, wherein the erection aid comprises
    an elastic stiffening band, said stiffening band comprising, in a longitudinal direction,
    a) an initial edge,
    b) an initial portion (IAA) adjoining the initial edge,
    c) a stiffening portion (IVA) adjoining the initial portion,
    d) a terminal portion (IEA) adjoining the stiffening portion, and
    e) a terminal edge adjoining the terminal portion, and having
        i) an upper edge adapted to come to rest in the sulcus (10) of the penis below the edge of the glans,
        ii) a lower edge adapted to come to rest near the root of the penis (14),
    and further having two faces adapted to form an outer face and an inner face,
    which stiffening band is stretchable in the longitudinal direction and wherein at least one of the faces of the elastic stiffening band is self-adhesive, the self-adhesive face being adapted to adhere to the skin of the penis and to the other face of the stiffening band solely by static friction, which stiffening band further comprises rigid reinforcements positioned in the stiffening portion, said rigid reinforcements extending between the upper edge and the lower edge of the stiffening band and being spaced apart from one another by elastic segments of the stiffening portion.

2. The erection aid of claim 1, wherein the rigid reinforcements are sewn to the stiffening portion, packed in pockets, glued on, or woven into the stiffening portion.

3. The erection aid of claim 1, wherein the rigid reinforcements have an extension in the longitudinal direction of the stiffening band which is equal to or greater than the elastic segments in the longitudinal direction of the stiffening band.

4. The erection aid of claim 3, wherein the extension of the rigid reinforcements in the longitudinal direction of the stiffening band is greater than the elastic segments in the longitudinal direction of the stiffening band so that the stiffening band appears uniform.

5. The erection aid of claim 1, comprising two rigid reinforcements (17) which are adapted to correspond in shape to the corpora cavernosa of the male member.

6. The erection aid of claim 1, wherein both of the faces of the stiffening band are self-adhesive.

7. The erection aid of claim 6, wherein the self-adhesive faces of the stiffening band have bristles (40, 41) or Velcro-like adhesion means protruding perpendicular to the faces, and the bristles or Velcro-like adhesion means of one face are adapted to mesh with those of the other face.

8. The erection aid of claim 1, further comprising a sheath (23) designed in form of a condom which is open at both ends, which sheath is adapted to cover the outer face of the stiffening band when said stiffening band is in the position for use.

9. The erection aid of claim 1, further comprising a sheath (23) designed in form of a condom which is open at both ends, a first half of which sheath being adapted to be located between the skin of the penis and the elastic stiffening band, and a second half of which sheath being adapted to be located on top of the stiffening band when the stiffening band is in the position for use.

10. The erection aid of claim 9, wherein the sheath (23), comprises two windings adapted to form the first and the second half of the sheath, which windings are wound in the opposite directions from one another, and wherein the the first winding corresponds to the first half of the sheath and the second winding corresponds to the second half of the sheath.

11. The erection aid of claim 1, further comprising a bracing part (42), which is joined to the elastic stiffening band permanently or detachably, and which is adapted to extend to the perineal region, which bracing part has an internal stabilizing element (19) which is bendable and which is adapted to support the weight of the penis, adapted to support the stiffening band on the perineum and adapted to keep the penis in a position corresponding to an erection.

12. The erection aid of claim 11, wherein the stabilizing element (19) in the bracing part is a metal inlay which can be bent at an angle of approximately 160°.

13. The erection aid of claim 1, further comprising an annular bracing part (37) which is adapted to embrace the root of the penis.

14. The erection aid of claim 13, wherein the annular bracing part (37) has one bearing face adapted to support the root of the penis, and one bearing face end adapted to support the stiffening band.

15. The erection aid of claim 13, wherein the annular bracing part (37) comprises a first section adapted to face the scrotal region and a second section adapted to face in the opposite direction of the first section, wherein the bracing part has a width which increases in the direction from the second section to the first section.

16. The erection aid of claim 13, wherein the annular bracing part (37) has a bracing elongation (39) that extends into the stiffening band.

17. The erection aid of claim 1, having a distance between the upper edge and the lower edge at the initial portion which is smaller than the distance between the upper edge and the lower edge in the stiffening portion and the terminal portion.

18. The erection aid of claim 17, wherein the distance between the upper edge and the lower edge of the initial portion increases continuously to the distance between the upper edge and the lower edge in the stiffening portion.

19. The erection aid of claim 1, wherein the initial portion of the stiffening band comprises an opening which opening forms a slit adapted to receive the initial edge and part of the initial portion, and wherein the distance between the initial edge and the opening is adapted to be greater than the circumference of the body of the penis.

20. The erection aid of claim 1, wherein the stiffening band has a narrow reinforcement on its upper and its lower edge.

21. The erection aid of claim 8, wherein the sheath is designed as a condom of conventional shape adapted to be rolled over onto the stiffening band, and wherein the sheath is perforated in the region adapted to surround the glans penis so that the closed end of the sheath can be torn off after the sheath has been applied.

22. The erection aid of claim 1, wherein the stiffening band is not stretchable in its longitudinal direction, wherein the faces of the stiffening band have a largely smooth surface, and which stiffening band is adapted to be disposed in spiral fashion on the body of the penis.

23. The erection aid of claim 22, wherein the stiffening band further comprises guide devices located on the initial and the terminal edge of the stiffening band.

24. An erection aid comprising a stiffening band which can be applied around the body of the penis of a user, two pieces of which are made of a bendable stiff material, which pieces are pivotably joined together along one side, and are to be secured detachably to one another on the free side by a retaining device to form a tube, which tube is adapted to encompass the body of the penis of a user, wherein the stiffening band further comprises, on the side that is adapted to face towards the body of the penis, small sacs, which sacs extend in the longitudinal direction of the tube axis, which sacs are adapted to be inflated by means of an air supply conduit comprising a valve.

* * * * *